(12) United States Patent
Ikeda et al.

(10) Patent No.: US 12,377,601 B2
(45) Date of Patent: Aug. 5, 2025

(54) FAST-ELUTING THREE-DIMENSIONALLY MOLDED OBJECT, FILAMENT FOR FAST-ELUTING THREE-DIMENSIONALLY MOLDED OBJECT, AND MATERIAL FOR FAST-ELUTING THREE-DIMENSIONALLY MOLDED OBJECT

(71) Applicant: ASTELLAS PHARMA INC., Tokyo (JP)

(72) Inventors: Sorato Ikeda, Tokyo (JP); Shota Hattori, Tokyo (JP); Masanori Kobayashi, Tokyo (JP)

( * ) Notice: Subject to any disclaimer, the term of this patent is extended or adjusted under 35 U.S.C. 154(b) by 22 days.

(21) Appl. No.: 18/113,482

(22) Filed: Feb. 23, 2023

(65) Prior Publication Data

US 2023/0202096 A1    Jun. 29, 2023

Related U.S. Application Data

(63) Continuation of application No. 16/088,041, filed as application No. PCT/JP2017/014205 on Apr. 5, 2017, now abandoned.

(30) Foreign Application Priority Data

Apr. 6, 2016    (JP) .................................. 2016-076810

(51) Int. Cl.
  *B29C 64/118*    (2017.01)
  *A61K 9/20*    (2006.01)
  (Continued)

(52) U.S. Cl.
  CPC .............. *B29C 64/118* (2017.08); *A61K 9/20* (2013.01); *A61K 31/506* (2013.01); *A61K 47/10* (2013.01);
  (Continued)

(58) Field of Classification Search
  None
  See application file for complete search history.

(56) References Cited

U.S. PATENT DOCUMENTS 6,187,342 B1    2/2001 Zeidler et al.
8,771,729 B2    7/2014 Perrett et al.
(Continued)

FOREIGN PATENT DOCUMENTS

AU    2012101357 A4 * 10/2012
JP    11512729 A    11/1999
(Continued)

OTHER PUBLICATIONS

U.S. Appl. No. 16/088,041, Non-Final Office Action mailed on Mar. 30, 2022, 21 pages.
(Continued)

*Primary Examiner* — Tae H Yoon
(74) *Attorney, Agent, or Firm* — MARSHALL, GERSTEIN & BORUN LLP

(57) ABSTRACT

Provided is a fast-eluting three-dimensionally molded object, which is formed by fused deposition modeling type three-dimensional molding and quickly elutes an active component. The fast-eluting three-dimensionally molded object is formed by the fused deposition modeling type three-dimensional molding and includes an active component, a water-soluble thermoplastic polymer, a water-soluble sugar and/or a water-soluble sugar alcohol, and a plasticizer component. The fast-eluting three-dimensionally molded object has an elution rate of the active component of 80% or higher within 85 minutes by a dissolution test method in the Japanese Pharmacopoeia, Sixteenth Edition.

13 Claims, 11 Drawing Sheets

(51) Int. Cl.
| | |
|---|---|
| A61K 31/506 | (2006.01) |
| A61K 47/10 | (2017.01) |
| A61K 47/26 | (2006.01) |
| A61K 47/32 | (2006.01) |
| A61K 47/34 | (2017.01) |
| B33Y 70/00 | (2020.01) |
| C08K 5/1545 | (2006.01) |
| C08L 29/04 | (2006.01) |
| C08L 33/14 | (2006.01) |
| C08L 39/06 | (2006.01) |
| B29K 29/00 | (2006.01) |
| B29K 33/04 | (2006.01) |
| B33Y 10/00 | (2015.01) |
| B33Y 80/00 | (2015.01) |

(52) U.S. Cl.
CPC .............. *A61K 47/26* (2013.01); *A61K 47/32* (2013.01); *A61K 47/34* (2013.01); *B33Y 70/00* (2014.12); *C08K 5/1545* (2013.01); *C08L 29/04* (2013.01); *C08L 33/14* (2013.01); *C08L 39/06* (2013.01); *A61K 9/2018* (2013.01); *A61K 9/2027* (2013.01); *A61K 9/2095* (2013.01); *B29K 2029/04* (2013.01); *B29K 2033/04* (2013.01); *B29K 2039/06* (2013.01); *B33Y 10/00* (2014.12); *B33Y 80/00* (2014.12)

(56) References Cited

U.S. PATENT DOCUMENTS

| | | |
|---|---|---|
| 2009/0004284 A1 | 1/2009 | Cheng et al. |
| 2010/0151011 A1 | 6/2010 | Benke |
| 2011/0236465 A1 | 9/2011 | Hall et al. |
| 2012/0213827 A1 | 8/2012 | Chatterji et al. |
| 2016/0066601 A1 | 3/2016 | Herr et al. |
| 2016/0177078 A1 | 6/2016 | Naito et al. |
| 2019/0217531 A1 | 7/2019 | Ikeda et al. |

FOREIGN PATENT DOCUMENTS

| | | |
|---|---|---|
| JP | 2004026750 A | 1/2004 |
| JP | 2009510138 A | 3/2009 |
| JP | 2013523634 A | 6/2013 |
| JP | 2014505714 A | 3/2014 |
| JP | 5751388 B1 | 5/2015 |
| WO | 2009069643 A1 | 6/2009 |
| WO | WO 2016/038356 A1 * | 3/2016 |

OTHER PUBLICATIONS

U.S. Appl. No. 16/088,041, Final Office Action mailed on Sep. 6, 2022, 13 pages.
U.S. Appl. No. 16/088,041, Final Office Action mailed on Dec. 6, 2021, 15 pages.
U.S. Appl. No. 16/088,041, Non-Final Office Action mailed on May 19, 2021, 12 pages.
U.S. Appl. No. 16/088,041, Non-Final Office Action mailed on Sep. 1, 2021, 13 pages.
European Application No. 17779170.4, Extended European Search Report mailed on Oct. 17, 2019, 6 pages.
Goyanes et al., 3D Printing of Modified-Release Aminosalicylate (4-ASA and 5-ASA) Tablets, European Journal of Pharmaceutics and Biopharmaceutics, vol. 89, Jan. 2015, pp. 157-162.
Goyanes et al., Effect of Geometry on Drug Release From 3D Printed Tablets, International Journal of Pharmaceutics, vol. 494, No. 2, 2015, pp. 657-663.
Goyanes et al., Fused-Filament 3D Printing (3DP) for Fabrication of Tablets, International Journal of Pharmaceutics, vol. 476, Nos. 1-2, Sep. 30, 2014, pp. 88-92.
International Application No. PCT/JP2017/014205, International Search Report and Written Opinion mailed on Jun. 13, 2017, 17 pages.
Pietrzak et al., A Flexible-Does Dispenser for Immediate and Extended Release 30 Printed Tablets, European Journal of Pharmaceutics and Biopharmaceutics, vol. 96, Oct. 2015, pp. 380-387.
Pietrzak, et al., A Flexible-Dose Dispenser for Immediate and Extended Release 3D printed Tablets, 2 Page of Abstract Only, European Journal of Pharmaceutics and Biopharmaceutics, vol. 96, Oct. 2015, 2 pages.
Sastry et al., Recent Technological Advances in Oral Drug Delivery—A Review, Pharmaceutical Science & Technology Today, vol. 3, No. 4, Apr. 1, 2000, pp. 138-145.
Yu et al., Novel Oral Fast-disintegrating Drug Delivery Devices with Predefined Inner Structure Fabricated by Three-dimensional Printing, Journal of Pharmacy and Pharmacology, vol. 61, No. 3, Mar. 1, 2009, pp. 323-329.

* cited by examiner

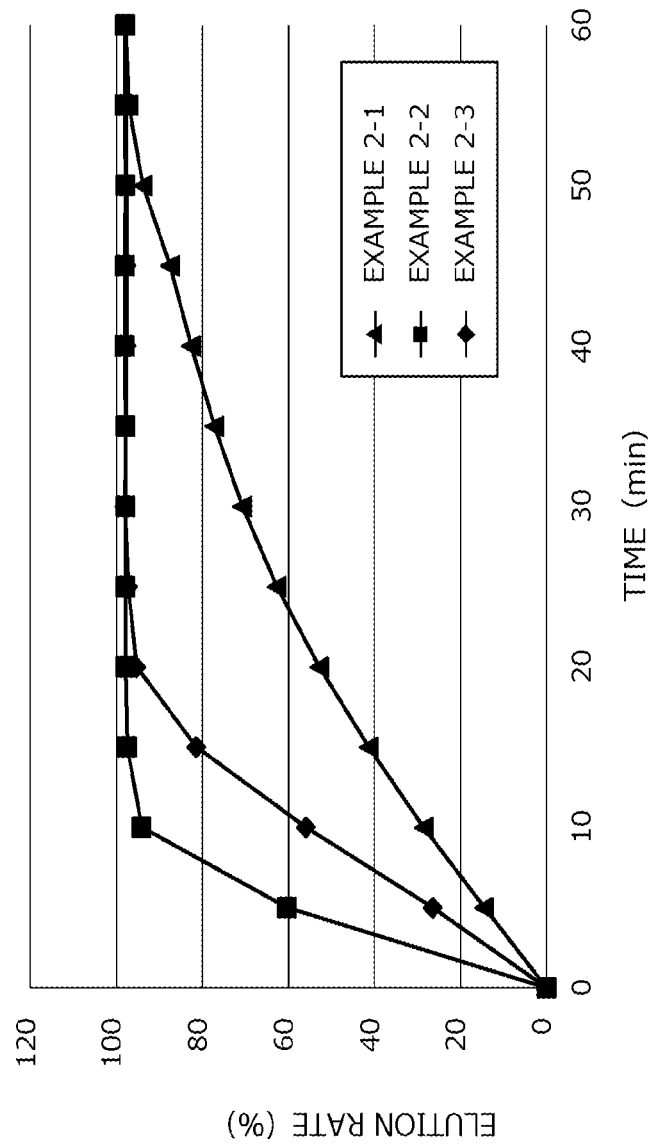

FAST-ELUTING THREE-DIMENSIONALLY MOLDED OBJECT, FILAMENT FOR FAST-ELUTING THREE-DIMENSIONALLY MOLDED OBJECT, AND MATERIAL FOR FAST-ELUTING THREE-DIMENSIONALLY MOLDED OBJECT

CROSS-REFERENCE TO RELATED APPLICATIONS

The present application is a continuation of U.S. application Ser. No. 16/088,041, filed Sep. 24, 2018, now abandoned, which is a 371 National Phase Application of PCT/JP2017/014205, filed Apr. 5, 2017, which claims priority to JP 2016-076810, filed Apr. 6, 2016, the disclosures of all of which are hereby incorporated by reference for all purposes.

TECHNICAL FIELD

The present invention relates to a fast-eluting three-dimensionally molded object, a filament for fast-eluting three-dimensionally molded object, and a material for fast-eluting three-dimensionally molded object. In particular, the present invention relates to a fast-eluting three-dimensionally molded object formed by fused deposition modeling type three-dimensional molding, a filament for fast-eluting three-dimensionally molded object for the fused deposition modeling, and a material for fast-eluting three-dimensionally molded object for the fused deposition modeling.

BACKGROUND ART

Conventionally, there has been known a 3D printing technique capable of molding a three-dimensionally molded object by three-dimensionally laminating and arranging a material for three-dimensionally molded object using 3D-CAD (computer-aided design) data created by a computer as a design plan.

The 3D printing technique can be classified into a plurality of groups mainly in accordance with a difference in a type of lamination. Examples of the 3D printing technique includes fused deposition modeling (FDM) in which a thermoplastic resin serving as a material for three-dimensionally molded object is thermally melted, extruded from a nozzle, and molded while being laminated on a molding stage and powder bed printing in which a powdery resin serving as a material for three-dimensionally molded object is laid over a molding stage and then a binder is sprayed on the powdery resin. Other techniques include stereolithography, powder selective laser sintering, and the like.

Under such circumstances, as the invention of a material for three-dimensionally molded object used in the fused deposition modeling, Patent literature 1, for example, discloses a material that develops little warpage and is easily subjected to surface polishing. It is disclosed that using such a material is advantageous for producing an industrial part having a new shape, confirming a design in a pre-production stage, and the like.

Moreover, recently, levetiracetam produced in a solid form using a 3D printer has been approved as a drug product under a name of SPRITAM (registered trademark) by U.S. Food and Drug Administration (FDA). As shown in such an example, the 3D printer is gaining attention as a new production method of a pharmaceutical preparation.

For example, Non patent literature 1 discloses an extended-release patient-tailored prednisolone tablet produced by the fused deposition modeling type three-dimensional molding.

It is disclosed that the prednisolone tablet includes a water-soluble thermoplastic polymer (a polyvinyl alcohol) as a base and has an elution rate of prednisolone serving as a pharmaceutically active component of 80% or higher in about 8 to 18 hours.

Further, for example, Non patent literature 2 discloses a tablet that is produced by the fused deposition modeling type three-dimensional molding and allows an adjustment of a drug dose.

It is disclosed that the tablet includes a polyvinyl alcohol as a base and has an elution rate of fluorescein serving as a model drug of 80% or higher in about 4.5 to 9 hours.

Further, for example, Non patent literature 3 discloses a tablet that is produced by the fused deposition modeling type three-dimensional molding and includes 4-aminosalicylic acid or 5-aminosalicylic acid in a modified-release formulation.

It is disclosed that the tablet includes a polyvinyl alcohol as a base and has an elution rate of 5-aminosalicylic acid of 80% or higher in about 1.5 to 2.5 hours.

CITATION LIST

Patent Literature

PATENT LITERATURE 1: JP 5751388 B1

Non Patent Literature

NON PATENT LITERATURE 1: European Journal of Pharmaceutical Sciences 68(2015) 11-17
NON PATENT LITERATURE 2: International Journal of Pharmaceutics 476(2014) 88-92
NON PATENT LITERATURE 3: European Journal of Pharmaceutics and Biopharmaceutics 89 (2015) 157-162

SUMMARY OF INVENTION

Technical Problem

It is generally considered that the fused deposition modeling and the powder bed printing are adopted to produce a solid object (a three-dimensionally molded object) using the 3D printer. However, when the production is performed by the powder bed printing, the strength of the three-dimensionally molded object becomes relatively weak, thereby causing a risk of breakage of the solid object, such as cracking and chipping, during a distribution process. Further, when the fused deposition modeling is adopted, the solid object hardly collapses, thereby causing a problem of reducing an elution rate of an active component.

Thus, it has been demanded to develop a solid object that elutes the active component relatively quickly while maintaining excellent injection moldability and printability by adopting the fused deposition modeling.

Specifically, it has been demanded to develop a fast-eluting solid object that is prepared so as to further increase the elution rate of the active component as compared to the solid object such as the one in Non patent literatures 1, 2, and 3.

Further, a technique capable of suitably performing the three-dimensional molding of the solid object has been demanded.

The present invention is made in light of the above-mentioned problems, and an object of the present invention is to provide a fast-eluting three-dimensionally molded object, which is formed by fused deposition modeling type three-dimensional molding and quickly elutes an active component.

Further, another object of the present invention is to provide a filament for fast-eluting three-dimensionally molded object and a material for fast-eluting three-dimensionally molded object used for forming the fast-eluting three-dimensionally molded object by the fused deposition modeling type three-dimensional molding.

Further, another object of the present invention is to provide the fast-eluting three-dimensionally molded object, the filament for fast-eluting three-dimensionally molded object, and the material for fast-eluting three-dimensionally molded object, which exhibit excellent injection moldability and printability in performing the three-dimensional molding by the fused deposition modeling.

Solution to Problem

The present inventors have conducted intensive studies and found that a three-dimensionally molded object that elutes an active component relatively quickly can be produced when a material for three-dimensionally molded object used for the fused deposition modeling type three-dimensional molding includes the active component, a water-soluble thermoplastic polymer, a water-soluble sugar and/or a water-soluble sugar alcohol, and a plasticizer component, thereby completing the present invention.

Further, the present inventors have found that the material for three-dimensionally molded object exhibits excellent injection moldability in producing the filament for three-dimensionally molded object and excellent printability in performing the three-dimensional molding by the fused deposition modeling, thereby completing the present invention.

Thus, according to the present invention, the above-mentioned problems can be solved by a three-dimensionally molded object, which is formed by fused deposition modeling type three-dimensional molding and includes an active component, a water-soluble thermoplastic polymer, a water-soluble sugar and/or a water-soluble sugar alcohol, and a plasticizer component.

Having the above configuration can achieve a fast-eluting three-dimensionally molded object.

Further, the three-dimensionally molded object that exhibits excellent injection moldability and printability can be achieve by performing the three-dimensional molding by the fused deposition modeling.

In the three-dimensionally molded object, an elution rate of the active component by a paddle method of a dissolution test method in the Japanese Pharmacopoeia, Sixteenth Edition, is preferably 80% or higher within 85 minutes.

Having the above configuration can achieve the fast-eluting three-dimensionally molded object.

In the three-dimensionally molded object, the water-soluble sugar and/or the water-soluble sugar alcohol has a glass transition temperature of preferably a room temperature or higher.

The water-soluble sugar and/or the water-soluble sugar alcohol is further preferably one or more kinds selected from the group consisting of sucrose, maltitol, xylitol, mannitol, erythritol, sorbitol, isomalt, and lactitol.

Further, the water-soluble sugar and/or the water-soluble sugar alcohol is preferably one or more kinds selected from the group consisting of maltitol, xylitol, mannitol, erythritol, sorbitol, isomalt, and lactitol.

Further, the water-soluble thermoplastic polymer is preferably one or more kinds selected from the group consisting of a polyvinyl alcohol, a polyvinyl caprolactam-polyvinyl acetate-polyethylene glycol graft copolymer, polyethylene oxide, polyvinylpyrrolidone, copolyvidone, a polyethylene glycol-polyvinyl alcohol-graft copolymer, a polyvinyl alcohol-acrylic acid-methyl methacrylate copolymer, aminoalkyl methacrylate copolymer RS, and aminoalkyl methacrylate copolymer E.

Further, the water-soluble thermoplastic polymer is preferably one or more kinds selected from the group consisting of a polyvinyl alcohol, polyvinylpyrrolidone, and aminoalkyl methacrylate copolymer E.

Further, it is preferable that the water-soluble thermoplastic polymer is one or more kinds selected from the group consisting of a polyvinyl alcohol, polyvinylpyrrolidone, and aminoalkyl methacrylate copolymer E and the water-soluble sugar and/or the water-soluble sugar alcohol is maltitol.

Further, the content of the water-soluble sugar and/or the water-soluble sugar alcohol is preferably 10 to 65 wt. % with respect to the total weight of the three-dimensionally molded object.

Further, the content of the water-soluble thermoplastic polymer is preferably 20 to 90 wt. % with respect to the total weight of the three-dimensionally molded object.

As for the water-soluble thermoplastic polymer, the water-soluble sugar and/or the water-soluble sugar alcohol, and the plasticizer component, optimizing each of these materials and the content thereof as described above can impart further excellent injection moldability and printability and achieve the three-dimensionally molded object adjustable to further increase the elution rate of the active component.

In the three-dimensionally molded object, the elution rate of the active component is preferably 80% or higher within 30 minutes.

Having the above configuration allows the production of the three-dimensionally molded object exhibiting further faster elutability as compared to the conventional three-dimensionally molded object.

The three-dimensionally molded object is preferably a ring-shaped solid object.

Having the above configuration can secure a larger surface area of the solid object as compared to the conventional cylinder or elliptical solid object, thus the elution of the active component in the solid object can be adjusted to be faster.

Further, a filament for fast-eluting three-dimensionally molded object and a material for fast-eluting three-dimensionally molded object used for forming a three-dimensionally molded object by fused deposition modeling type three-dimensional molding can be achieved by including an active component, a water-soluble thermoplastic polymer, a water-soluble sugar and/or a water-soluble sugar alcohol, and a plasticizer component.

Advantageous Effects of Invention

According to the present invention, there can be provided the fast-eluting three-dimensionally molded object, which is formed by the fused deposition modeling type three-dimensional molding and quickly elutes the active component.

Further, there can be provided the filament for fast-eluting three-dimensionally molded object and the material for fast-eluting three-dimensionally molded object used for forming the fast-eluting three-dimensionally molded object by the fused deposition modeling type three-dimensional molding.

Further, there can be provided the fast-eluting three-dimensionally molded object, the filament for fast-eluting three-dimensionally molded object, and the material for fast-eluting three-dimensionally molded object, which exhibit excellent injection moldability and printability in performing the three-dimensional molding by the fused deposition modeling.

BRIEF DESCRIPTION OF DRAWINGS

FIG. 3 is result data of the elution test using the solid objects having different shapes in Test example 2.

DESCRIPTION OF EMBODIMENTS

Figure 1:
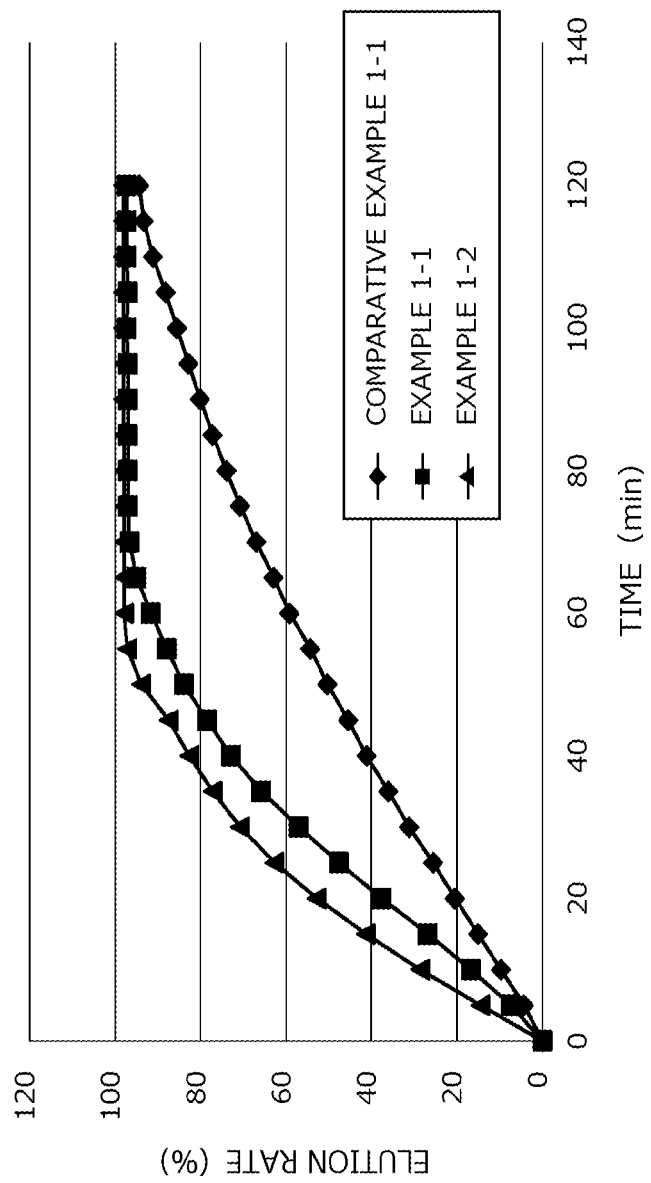
FIG. 1 is result data of an elution test in Test example 1.

The following describes embodiments of the present invention with reference to FIG. 1 to FIG. 11.

The present embodiments relate to the invention of a fast-eluting three-dimensionally molded object, which is formed by fused deposition modeling type three-dimensional molding and characterized by including a pharmaceutically active component, a polyvinyl alcohol, maltitol, and triethyl citrate.

Further, the present embodiments relate to the invention of a filament for fast-eluting three-dimensionally molded object and a material for fast-eluting three-dimensionally molded object used for forming the fast-eluting three-dimensionally molded object described above.

The term "material for three-dimensionally molded object" refers to a fast-eluting material, which is suitably used for the three-dimensional molding, in particular, for the fused deposition modeling, and includes a component that can be used for oral administration, oral ingestion, intraoral administration, intrarectal administration, or vaginal administration.

The material for three-dimensionally molded object is, for example, formed in a powder shape and obtained by appropriately formulating each constituent component, however, the shape can be changed without a particular limitation. For example, the powder obtained by formulating each constituent component may be granulated to form a pellet.

The term "filament for three-dimensionally molded object" refers to a product obtained by subjecting the material for three-dimensionally molded object to melt-kneading with compression and extrusion molding using an extruding machine (an extruder) or the like. The filament for three-dimensionally molded object is formed, for example, as a filamentous body having a diameter of about 1.0 to 3.0 mm.

The term "three-dimensionally molded object" refers to a product obtained by thermally melting the filament for three-dimensionally molded object, extruding the melted filament from a nozzle, and molding the melted filament layer by layer on a molding stage using a fused deposition modeling type 3D printing apparatus.

An administration route of the three-dimensionally molded object is not particularly limited. Examples of the administration route include oral administration or oral ingestion, intraoral administration, intrarectal administration, vaginal administration, and the like. Oral administration is preferable.

The three-dimensionally molded object is not limited to a pharmaceutical and may be, for example, a solid food for oral ingestion, such as a food for specified health uses, a food with nutrient function claims, a food with function claims, and a supplement.

The three-dimensionally molded object is preferably formed in a ring shape. However, the shape may be changed without a particular limitation. The three-dimensionally molded object may be formed in a conventional cylinder or elliptical shape.

Next, each constituent component of the material for three-dimensionally molded object will be described.

The material for three-dimensionally molded object includes an active component, a water-soluble thermoplastic polymer, a water-soluble sugar and/or a water-soluble sugar alcohol, and a plasticizer component.

Note that the material for three-dimensionally molded object may further include various additive components. For example, one or more of a binder, a stabilizer, a disintegrating agent, a disintegrating assistant, an acidulant, a foaming agent, an artificial sweetener, a flavoring agent, a lubricant, a coloring agent, a buffer, an antioxidant, a surfactant, and the like may be combined and suitably included in an appropriate amount.

The term "active component" refers to a material that exhibits physiological activity included in a pharmaceutical agent, a quasi-drug, a health food, and the like. The active component serving as an active component of the three-dimensionally molded object is not particularly limited as long as it is stable after thermally melted. For example, the active component may be a pharmaceutical. In another embodiment, the active component may be the one included in a food for specified health uses, a food with nutrient function claims, a food with function claims, a supplement, and the like. The pharmaceutically active component used as the active component is preferably poorly water soluble.

However, the pharmaceutically active component is not particularly limited to the one described above, and may be water insoluble or water soluble. The pharmaceutically active component may be an active component included in a food for specified health uses, a food with nutrient function claims, a food with function claims, a supplement, and the like.

The content of the active component of the material for three-dimensionally molded object (the filament for three-dimensionally molded object, the three-dimensionally molded object) is 0.1 to 40 wt. %, preferably 0.1 to 20 wt. %, with respect to the total weight of the material for three-dimensionally molded object (the filament for three-dimensionally molded object, the three-dimensionally molded object). However, the content may be changed without a particular limitation within a range capable of achieving the effect of the present invention.

The term "thermoplastic polymer" refers to a polymer material which has thermoplasticity, that is, a property causing a material to be hardly deformable at a normal temperature, but freely deformable due to plasticity upon appropriate heating and rigid again upon cooling. The thermoplastic polymer serves as a base of the three-dimensionally molded object and imparts excellent injection moldability and printability (plasticity). The thermoplastic polymer is preferably water soluble in order to increase elutability of the active component into water.

Specifically, the thermoplastic polymer is preferably one or more kinds selected from the group consisting of a polyvinyl alcohol, a polyvinyl caprolactam-polyvinyl acetate-polyethylene glycol graft copolymer, polyethylene oxide, polyvinylpyrrolidone, copolyvidone, a polyethylene glycol-polyvinyl alcohol-graft copolymer, a polyvinyl alcohol-acrylic acid-methyl methacrylate copolymer, aminoalkyl methacrylate copolymer RS, and aminoalkyl methacrylate copolymer E.

For example, the thermoplastic polymer may be one or more kinds selected from the group consisting of a polyvinyl alcohol, polyvinylpyrrolidone, a polyethylene glycol-polyvinyl alcohol-graft copolymer, and aminoalkyl methacrylate copolymer E. The thermoplastic polymer is preferably one or more kinds selected from the group consisting of a polyvinyl alcohol, polyvinylpyrrolidone, and aminoalkyl methacrylate copolymer E.

The polyvinyl alcohol is more preferable from the viewpoint of printability.

Further, using the polyvinyl alcohol as the thermoplastic polymer allows the preparation of the filament having high plasticity and more strength.

In a case where the polyvinyl alcohol is used as the water-soluble thermoplastic polymer, the polyvinyl alcohol is preferably a polymer compound that has high water solubility, a relatively small average molecular weight (average polymerization degree), and a relatively small saponification rate.

Specifically, the polyvinyl alcohol has the average molecular weight of 20,000 (the average polymerization degree of 400) or less, preferably 10,000 (the average polymerization degree of 200) or less, more preferably 6,000 (the average polymerization degree of 120) or less. Further, the polyvinyl alcohol has the saponification rate of 90.0 mol % or less, preferably 80.0 mol % or less.

The content of the water-soluble thermoplastic polymer is 20 to 90 wt. %, preferably 20 to 80 wt. %, more preferably 20 to 40 wt. %, with respect to the total weight of the material for three-dimensionally molded object (the filament for three-dimensionally molded object, the three-dimensionally molded object). However, the content may be changed without a particular limitation within a range capable of achieving the effect of the present invention.

The term "water-soluble sugar and/or water-soluble sugar alcohol" refers to a component that imparts excellent plasticity, improves injection moldability and printability, increases elutability of the active component into water, and the like.

For example, the sugar alcohol that hardly causes caramelization and a Maillard reaction by heat is preferable for maintaining excellent injection moldability and excellent extrudability and printability during the three-dimensional molding. For example, the sugar alcohol may have a glass transition temperature of a room temperature (1 to 30° C.) or higher, preferably 40° C. or higher, according to the Japanese Pharmacopoeia, Sixteenth Edition.

The "water-soluble sugar and/or water-soluble sugar alcohol" is desirably one or more kinds of sugar alcohols selected from the group consisting of maltitol, xylitol, mannitol, erythritol, sorbitol, isomalt, and lactitol, preferably one or more kinds of sugar alcohols selected from the group consisting of maltitol, isomalt, and lactitol. Maltitol is more preferable.

However, the water-soluble sugar and/or the water-soluble sugar alcohol may be changed without being particularly limited to the above within a range capable of achieving the effect of the present invention. For example, sucrose or the like may be used as the sugar.

The content of the water-soluble sugar and/or the water-soluble sugar alcohol is 10 to 65 wt. %, preferably 10 to 60 wt. %, more preferably 20 to 65 wt. %, further preferably 20 to 60 wt. %, particularly preferably 35 to 55 wt. %, particularly preferably 20 to 55 wt. %, with respect to the total weight of the material for three-dimensionally molded object (the filament for three-dimensionally molded object, the three-dimensionally molded object). However, the content may be changed without a particular limitation within a range capable of achieving the effect of the present invention.

The term "plasticizer component" refers to a component serving as a plasticizer in the filament for three-dimensionally molded object and the three-dimensionally molded object, and the plasticizer component is added to maintain excellent injection moldability and printability.

Specifically, the plasticizer is desirably one or more kinds selected from the group consisting of triethyl citrate, macrogol, triacetin, a medium-chain fatty acid triglyceride, a polyoxyethylene polyoxypropylene block copolymer, and castor oil. Triethyl citrate is preferable.

However, the plasticizer component may be changed without being particularly limited to the above within a range capable of achieving the effect of the present invention.

The content of the plasticizer component is 1 to 30 wt. %, preferably 1 to 10 wt. %, more preferably 1 to 5 wt. %, with respect to the total weight of the material for three-dimensionally molded object (the three-dimensionally molded object). However, the content may be changed without a particular limitation within a range capable of achieving the effect of the present invention.

Next, a production method of the three-dimensionally molded object (the solid object) will be described. Note that the present invention is not particularly limited to the present production method.

The production method of the three-dimensionally molded object of the present embodiment sequentially performs:

a material mixing step in which the water-soluble thermoplastic polymer, the active component, the water-soluble sugar and/or the water-soluble sugar alcohol, and the plasticizer component are mixed to obtain the material for three-dimensionally molded object;

a compressing and melt-kneading step in which the material for three-dimensionally molded object is melt-kneaded while being compressed;

a filament producing step in which the material for three-dimensionally molded object, which has been compressed and melt-kneaded, is subjected to injection molding, and then wound up with a winder to produce the filament; and a molding step in which the filament is thermally melted, extruded from a nozzle, and laminated on a molding stage to mold the three-dimensionally molded object.

That is, in the production method of the three-dimensionally molded object, first, in the material mixing step, the active component, the water-soluble thermoplastic polymer, the water-soluble sugar and/or the water-soluble sugar alcohol, and the plasticizer component are each mixed in a predetermined formulation ratio using a mixer to obtain the material for three-dimensionally molded object.

Then, the material for three-dimensionally molded object thus obtained is melt-kneaded while been compressed under a predetermined pressure using a known extruding machine (e.g., an extruder) in the compressing and melt-kneading step. After melt-kneading, injection molding is performed using a molder and an injection-molded object is wound up with an automatic winder to obtain the filament for three-dimensionally molded object in the filament producing step.

Note that it is desirable that a melting temperature is set to 120 to 200° C., preferably 140 to 170° C., for suitably melt-kneading the material for three-dimensionally molded object in the extruding machine. Further, it is desirable that the rotation number of barrel is increased to 100 to 200 rpm during kneading and decreased to 5 to 30 rpm during injection molding. Further, it is desirable that melt-kneading time is set to 3 to 15 minutes.

Then, in the molding step, the filament for three-dimensionally molded object thus obtained is thermally melted, extruded from a nozzle, and molded while being laminated on a molding stage using a known fused deposition modeling type 3D printing apparatus to obtain the three-dimensionally molded object.

Note that it is desirable that a nozzle temperature is set to 80 to 250° C., preferably 110 to 200° C., more preferably 150° C. or 160° C. or higher and 250° C. or 200° C. or lower, for suitably extruding the filament for three-dimensionally molded object from the nozzle.

As described above, when the three-dimensionally molded object is produced by using the material for three-dimensionally molded object (the filament for three-dimensionally molded object) of the present invention, it becomes possible to form the solid object that exhibits excellent injection moldability and printability (plasticity) as well as fast elutability adjusted to increase the elution rate of the pharmaceutically active component.

Here, the term "injection moldability" will be described. First, the filament for three-dimensionally molded object needs to be molded into a fixed thickness. A reason for this is that if a diameter of the molded filament is uneven, an extrusion amount from the 3D printing apparatus becomes uneven, thereby easily causing a printing failure. Further, after injection molding, the filament needs to be solidified relatively quickly. A reason for this is that the slow solidification results in the filament of uneven thickness.

Further, the term "printability" will be described. First, the filament for three-dimensionally molded object needs to be inserted into a silicon tube attached to the 3D printing apparatus for setting the filament to the 3D printing apparatus. This operation requires the filament to be flexible enough to be bent to some extent (the filament can be set to the apparatus if the filament is bendable at least when heated). Further, the filament needs to have enough plasticity not to be broken when it is suitably bent to be set to the apparatus. A reason for this is that if the filament has low plasticity and is thus fragile, a part of the filament is chipped, thereby causing a gap, which makes it difficult to perform stable printing. Further, after the filament is melted at a tip of the nozzle of the 3D printing apparatus, a melted material needs to be extruded by a fixed amount.

Using the material for three-dimensionally molded object of the present invention gives a good result in injection moldability and printability and makes it possible to form a desired three-dimensionally molded object.

Further, the term "three-dimensionally molded object exhibiting fast elutability" will be described. In the present invention, according to a paddle method (the paddle rotation number: 50 rpm) of a dissolution test method in the Japanese Pharmacopoeia, Sixteenth Edition, the elution rate of the active component in the solid object is 80% or higher within 120 minutes, preferably 80% or higher within 85 minutes, more preferably 80% or higher within 60 minutes, further preferably 80% or higher within 30 minutes, particularly preferably 85% or higher within 30 minutes, particularly preferably 90% or higher within 30 minutes, particularly preferably 85% or higher within 15 minutes. An upper limit of the elution rate is 100%. As a test solution used in the dissolution test, for example, a dissolution test 1st fluid, water, or the like may be used.

Using the material for three-dimensionally molded object of the present invention makes it possible to form a fast-eluting solid object that quickly elutes the active component.

EXAMPLE

Examples of the present invention will be described in detail below. Note that the present invention is not limited to the present examples.

Example 1: Three-Dimensionally Molded Objects Having Different Formulation Ratios of Maltitol A filament was prepared using a material for three-dimensionally molded object having a formulation ratio shown in Table 1 with a extruder equipped with an injection molder, Xplore (registered trademark, manufactured by DSM) and then a solid object serving as a three-dimensionally molded object was produced using a fused deposition modeling type 3D printing apparatus, Eagleed (registered trademark, manufactured by Reis Enterprise Co., Ltd).

As specific materials, $N^2$-[(2E)-3-(4-chlorophenyl)-2-propenoyl]-N-[2-oxo-2-(4-{[6-(trifluoromethyl)pyrimidine-4-yl]oxy}piperidine-1-yl)ethyl]-3-pyridine-2-yl-L-alaninamide (manufactured by Astellas Pharma Inc., a solubility to a dissolution test 1st fluid of the Japanese Pharmacopoeia: >100□M, a solubility to a dissolution test 2nd fluid of the Japanese Pharmacopoeia: 23.2□M, hereinafter abbreviated as a compound A) was selected as an active component, Poly(vinyl alcohol) [MW 6000] (manufactured by Polysciences, Inc., the same hereinafter unless otherwise specified) was selected as a thermoplastic polymer, maltitol (SweetPearl P200, manufactured by Roquette, the same hereinafter unless otherwise specified) was selected as a sugar alcohol, and Triethyl Citrate (manufactured by Tokyo Chemical Industry Co., Ltd., the same hereinafter unless otherwise specified) was selected as a plasticizer component.

Further, a formulation ratio of maltitol was set to 0 wt. % in a sample of maltitol 0 wt. % in Comparative example 1-1, a formulation ratio of maltitol was set to 35 wt. % in a sample of maltitol 35 wt. % in Example 1-1, and a formulation ratio of maltitol was set to 55 wt. % in a sample of maltitol 55 wt. % in Example 1-2 to produce the solid objects (n=2).

Each solid object in Examples 1-1 and 1-2 and Comparative example 1-1 was formed in a cylinder shape, and setting values of 3D CAD data were set such that height of each solid object became 1.5 mm and a diameter of each solid object became 12.0 mm.

TABLE 1

| | | SOLID OBJECTS | | |
|---|---|---|---|---|
| | | COMPARATIVE EXAMPLE 1-1 MALTITOL 0 wt. % | EXAMPLE 1-1 MALTITOL 35 wt. % | EXAMPLE 1-2 MALTITOL 55 wt. % |
| EACH CONSTITUENT COMPONENT (wt. %) | COMPOUND A | 20 | 20 | 20 |
| | POLYVINYL ALCOHOL | 79 | 40 | 20 |
| | MALTITOL | 0 | 35 | 55 |
| | TRIETHYL CITRATE | 1 | 5 | 5 |
| WEIGHT OF SOLID OBJECT (mg) Average(n = 2) | | 208 | 239 | 222 |
| HEIGHT OF SOLID OBJECT (mm) Average(n = 2) | | 1.6 | 1.6 | 1.6 |

Test Example 1: Elution Test of Active Component

An elution test was performed using the solid objects in Examples 1-1 and 1-2 and Comparative example 1-1 shown in Table 1 in accordance with the paddle method (the paddle rotation number: 50 rpm (revolution per minute)) of the dissolution test method in the Japanese Pharmacopoeia, Sixteenth Edition.

As a test liquid, 900 ml of the dissolution test 1st fluid was used and an elution rate of the active component (the compound A) after starting the test was evaluated by an ultraviolet-visible spectroscopic method (a UV-VIS method).

Example 2: Three-Dimensionally Molded Objects Having Different Shapes

Figure 2A:
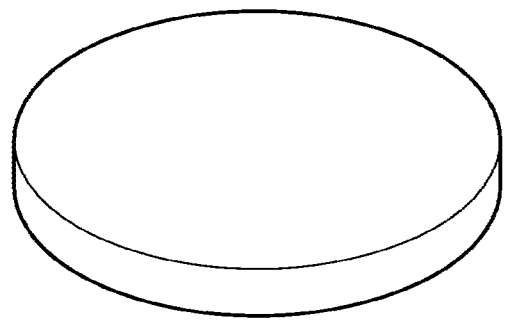
FIG. 2A is a perspective view illustrating a solid object (in a cylinder shape) in Example 2-1.

As the three-dimensionally molded objects having different shapes, a total of three kinds of the solid objects (n=2) were produced as follows: a cylinder shape shown in FIG. 2A (Example 2-1), a ring shape 1 shown in FIG. 2B (Example 2-2), and a ring shape 2 shown in FIG. 2C (Example 2-3).

A formulation ratio of each constituent component was adjusted such that the compound A as the active component became 20 wt. %, the polyvinyl alcohol became 20 wt. %, maltitol became 55 wt. %, and triethyl citrate became 5 wt. % with respect to 100 wt. % of the total weight.

TABLE 2

| | SOLID OBJECTS | | |
|---|---|---|---|
| SHAPES OF SOLID OBJECTS | EXAMPLE 2-1 CYLINDER SHAPE | EXAMPLE 2-2 RING SHAPE 1 | EXAMPLE 2-3 RING SHAPE 2 |
| 3D CAD DATA SETTING VALUES | DIAMETER 12.0 mm | OUTER DIAMETER 12.0 mm INNER DIAMETER 7.6 mm | OUTERMOST CIRCLE OUTER DIAMETER 12.0 mm OUTERMOST CIRCLE INNER DIAMETER 10.0 mm INTERMEDIATE CIRCLE OUTER DIAMETER 8.0 mm INTERMEDIATE CIRCLE INNER DIAMETER 6.0 mm INNERMOST CIRCLE OUTER DIAMETER 4.0 mm INNERMOST CIRCLE INNER DIAMETER 2.0 mm |
| WEIGHT OF SOLID OBJECT (mg) Average(n = 2) | 222 | 281 | 263 |
| HEIGHT OF SOLID OBJECT(mm) Average(n = 2) | 1.6 | 2.7 | 2.6 |

(Results and Discussion of Test Example 1)

On the basis of analysis of test results, a graph in FIG. 1 shows a relation between "time (min) after starting test" and "elution rate (%) of active component" of the solid object in each Example.

The solid object in Example 1-1 showed an average elution rate of 87.9% after the lapse of 55 minutes.

The solid object in Example 1-2 showed an average elution rate of 87.5% after the lapse of 45 minutes.

From the results in Test example 1, it was found that formulation of maltitol caused fast elution. Further, it was found that increasing the formulation ratio of maltitol caused further faster elution of the active component.

Test Example 2: Elution Test of Active Component

The elution test was performed using the solid objects in Examples 2-1 to 2-3 in the same manner as in Test example 1 in accordance with the paddle method (the paddle rotation number: 50 rpm) of the dissolution test method in the Japanese Pharmacopoeia, Sixteenth Edition.

(Results and Discussion of Test Example 2)

On the basis of analysis of test results, a graph in FIG. 3 shows a relation between the "time (min) after starting test" and the "elution rate (%) of active component" of the solid object in each of Examples 2-1 to 2-3.

From the results in Test example 2, the solid object formed in the cylinder shape in Example 2-1 showed the average elution rate of 87.5% after the lapse of 45 minutes, the solid object formed in the ring shape 1 in Example 2-2 showed the average elution rate of 95.3% after the lapse of 20 minutes, and the solid object formed in the ring shape 2 in Example 2-3 showed the average elution rate of 94.1% after the lapse of 10 minutes.

Further, selecting the ring shapes in Examples 2-2 and 2-3 having larger surface areas caused further faster elutability.

Example 3: Three-Dimensionally Molded Object Including 100 mg of Active Component As the three-dimensionally molded object including 100 mg of the active component, the solid object in Example 3 having a shape and a formulation ratio shown in Table 3 was produced.

Figure 2B:
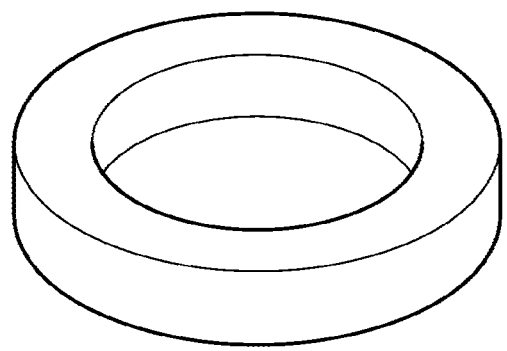
FIG. 2B is a perspective view illustrating a solid object (in a ring shape 1) in Example 2-2.
Figure 2C:
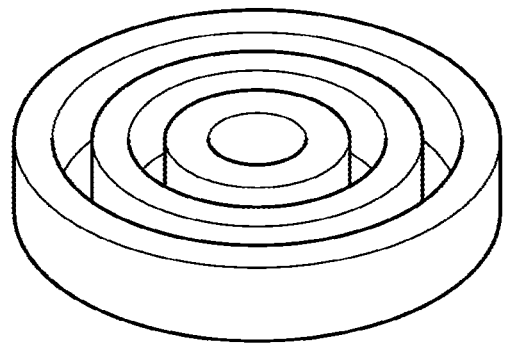
FIG. 2C is a perspective view illustrating a solid object (in a ring shape 2) in Example 2-3.

Note that the ring shape 1 shown in FIG. 2B was selected as the shape in Example 3 and a formulation ratio of each constituent component was adjusted such that the compound A as the active component became 20 wt. %, the polyvinyl alcohol became 20 wt. %, maltitol became 55 wt. %, and triethyl citrate became 5 wt. % with respect to 100 wt. % of the total weight.

TABLE 3

|  |  | EXAMPLE 3 |
|---|---|---|
| EACH CONSTITUENT COMPONENT (wt. %) | COMPOUND A | 20 |
|  | POLYVINYL ALCOHOL | 20 |
|  | MALTITOL | 55 |
|  | TRIETHYL CITRATE | 5 |
|  | TOTAL (wt. %) | 100 |
|  | 3D CAD DATA SETTING VALUES | RING SHAPE 1 OUTER DIAMETER 12.0 mm INNER DIAMETER 7.6 mm |
|  | WEIGHT OF SOLID OBJECT (mg)(n = 1) | 482 |
|  | HEIGHT OF SOLID OBJECT (mm)(n = 1) | 4.6 |

Test Example 3: Elution Test of Active Component

The elution test was performed using the solid object in Example 3 shown in Table 3 in the same manner as in Test example 1 in accordance with the paddle method (the paddle rotation number: 50 rpm) of the dissolution test method in the Japanese Pharmacopoeia, Sixteenth Edition.

(Results and Discussion of Test Example 3)

Figure 4:
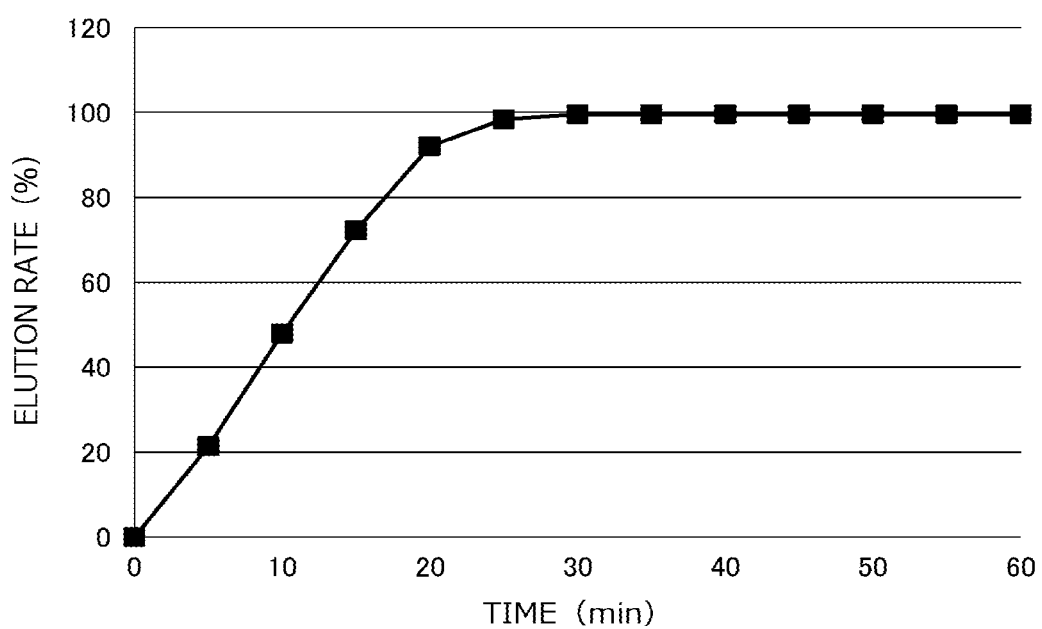
FIG. 4 is result data of the elution test in Test example 3.

On the basis of analysis of results of the elution test, a graph in FIG. 4 shows a relation between the "time (min) after starting test" and the "elution rate (%) of active component" of the solid object in Example 3.

From the results in Test example 3, the solid object in Example 3 showed the elution rate of 92.0% after the lapse of 20 minutes.

Test Example 4: Evaluation Test of Oral Absorbability in Dog

A test for evaluating oral absorbability in a dog was performed using the solid object in Example 3.

Specifically, the solid object in Example was used as an administration sample and the solid object in Example 3 was orally administered to a dog with a small amount of water. Blood was collected at a total of 8 time points of 0.25, 0.5, 1, 2, 4, 6, 8, and 24 hours post oral administration. Subsequently, a drug concentration in blood plasma obtained by centrifugal separation was measured using a liquid chromatographic mass spectrometer. Note that four dogs (n=4) were prepared in the present test.

Note that, as for intake of food and water, the dogs were fasted from 16 hours before administration of the solid object in Example 3 until completion of the blood collection at 8 hours after administration of the solid object. Further, the dogs were restricted from water from 30 minutes before administration until completion of the blood collection at 2 hours after administration.

For adjusting pH in stomach, intramuscular administration of pentagastrin (0.015 mg/kg) was performed at 30 minutes before administration of the solid object in Example 3, and 30 and 90 minutes after administration of the solid object.

In a detail of the administration method, water is administered by a catheter immediately after administration of the solid object to obtain a total administration liquid amount of up to 50 ml.

(Results and Discussion of Test Example 4)

Figure 5:
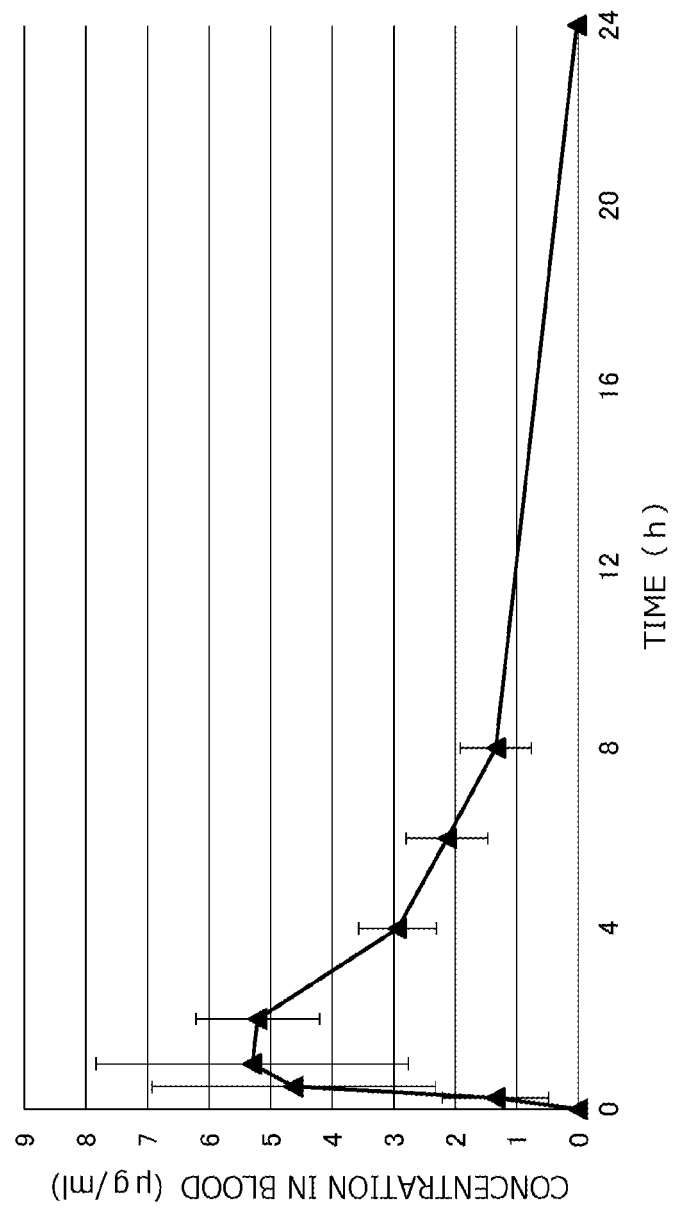
FIG. 5 is result data of an oral absorbability test in a dog in Test example 4.

On the basis of analysis of test results, a graph in FIG. 5 shows a relation between "time (h) after oral administration" and "concentration in blood plasma ($\mu$g/ml)" of the solid object in Example 3.

Further, "Cmax ($\mu$g/ml)", "Tmax (h)" and "AUC$^{0-24}$ ($\mu$g·h/ml)" were obtained on the basis of the graph in FIG. 5 and shown in Table 4.

TABLE 4

|  | EXAMPLE 3 |
|---|---|
| Cmax($\mu$g/ml) | 5.6 ± 1.8 |
| Tmax(h) | 1.2 ± 0.8 |
| AUC$^{0-24}$($\mu$g · h/ml) | 35.1 ± 11.1 |

Note that "Cmax ($\mu$g/ml)" represents a maximum concentration in the blood plasma and "Tmax (h)" represents a time required for reaching the maximum concentration in the blood plasma (a time required for reaching Cmax).

"AUC$^{0-24}$ ($\mu$g·h/ml)" represents an area under the blood plasma drug concentration-time curve from the time of oral administration to 24 hours after oral administration.

In Example 3, Tmax was 1.2±0.8 (h) and AUC was 35.1±11.1 ($\mu$g·h/ml), thus it could be said that the solid object of the present invention exhibited a performance of quickly releasing a drug in vivo.

From the results in Test examples 1 to 4, it was found that when the three-dimensionally molded object was prepared using the material for three-dimensionally molded object (the filament for three-dimensionally molded object) in each Example of the present invention, the fast-eluting solid object having excellent injection moldability and printability (plasticity) could be produced.

Example 4: Three-Dimensionally Molded Objects Including Various Sugars and Sugar Alcohols The filaments having formulation and formulation ratios shown in Table 5 were produced and the solid objects in Examples 4-1 to 4-8 (n=3) were produced using these filaments with the 3D printer as the three-dimensionally molded objects each including 50 mg of the active component.

Note that the ring shape 1 shown in FIG. 2B was selected as the shape in Examples 4-1 to 4-8 and printing was performed on the basis of 3D CAD data in which an outer diameter of the ring was set to 12.0 mm and an inner diameter of the ring was set to 7.6 mm. A formulation ratio of each constituent component was adjusted such that the compound A as the active component became 20 wt. %, the polyvinyl alcohol became 40 wt. %, the water-soluble sugar and/or the water-soluble sugar alcohol became 35 wt. %, and triethyl citrate became 5 wt. % with respect to 100 wt. % of the total weight.

Note that, as the sugar or the sugar alcohol, other than the same maltitol as used in Example 1, xylitol (product name: xylitol, manufactured by Wako Pure Chemical Industries, Ltd.), mannitol (product name: Pearlitol 200SD, manufactured by Roquette), lactitol (product name: lactitol monohydrate, manufactured by Wako Pure Chemical Industries, Ltd.), sucrose (product name: sucrose, manufactured by Wako Pure Chemical Industries, Ltd.), erythritol (product name: erythritol 100M, manufactured by B Food Science Co., Ltd.), sorbitol (product name: sorbitol, manufactured by KANTO CHEMICAL Co., Inc.), and isomalt (product name: Galen IQ720, manufactured by BENEO-Palatinit GmbH) were used.

Test Example 5: Elution Test of Active Component

The elution test was performed using the solid objects in Examples 4-1 to 4-8 in the same manner as in Test example 1 in accordance with the paddle method (the paddle rotation number: 50 rpm) of the dissolution test method in the Japanese Pharmacopoeia, Sixteenth Edition.

(Results and Discussion of Test Example 5)

Figure 6:
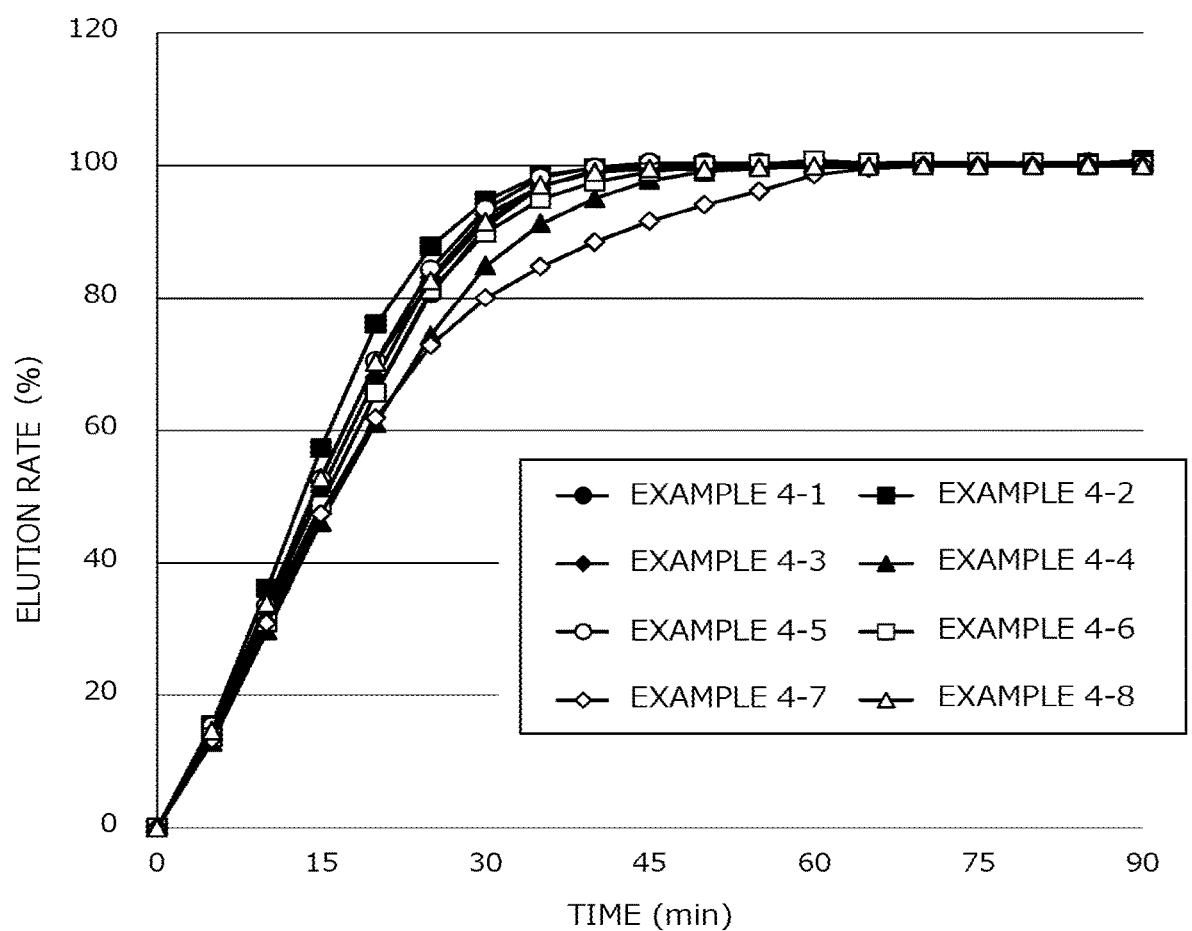
FIG. 6 is result data of the elution test in Test example 5.

On the basis of analysis of results of the elution test, a graph in FIG. 6 shows a relation between the "time (min) after starting test" and the "elution rate (%) of active component" of the solid object in each of Examples 4-1 to 4-8.

From the results in Test example 5, the solid objects in Examples 4-1 to 4-8 showed the elution rates after the lapse of 30 minutes as follows: 91% (Example 4-1: maltitol), 95% (Example 4-2: xylitol), 93% (Example 4-3: mannitol), 85% (Example 4-4: lactitol), 93% (Example 4-5: sucrose), 90% (Example 4-6: erythritol), 80% (Example 4-7: sorbitol), and 92% (Example 4-8: isomalt).

Example 5: Three-Dimensionally Molded Objects Including Different Active Components The filaments having formulation and formulation ratios shown in Table 6 were produced and the solid objects in Examples 5-1 and 5-2 (n=3) were produced with the 3D printer as the three-dimensionally molded objects each including 50 mg of the active component. In Example 5-1, acetaminophen (product name: pharmacopoeia acetaminophen, manufactured by YAMAMOTO Corp.) was formulated as the active component and, in Example 5-2, theophylline (product name: Theophylline, manufactured by Tokyo Chemical Industry Co., Ltd.) was formulated as the active component.

Note that the ring shape 1 shown in FIG. 2B was selected as the shape in Examples 5-1 and 5-2 and printing was performed on the basis of 3D CAD data in which an outer diameter of the ring was set to 12.0 mm and an inner diameter of the ring was set to 7.6 mm. A formulation ratio of each constituent component was adjusted such that the active component became 20 wt. %, the polyvinyl alcohol became 40 wt. %, maltitol became 35 wt. %, and triethyl citrate became 5 wt. % with respect to 100 wt. % of the total weight.

TABLE 5

| | | EXAMPLE 4-1 MALTITOL | EXAMPLE 4-2 XYLITOL | EXAMPLE 4-3 MANNITOL | EXAMPLE 4-4 LACTITOL | EXAMPLE 4-5 SUCROSE | EXAMPLE 4-6 ERYTHRITOL | EXAMPLE 4-7 SORBITOL | EXAMPLE 4-8 ISOMALT |
|---|---|---|---|---|---|---|---|---|---|
| EACH CONSTITUENT COMPONENT (wt %) | COMPOUND A | 20 | 20 | 20 | 20 | 20 | 20 | 20 | 20 |
| | POLYVINYL ALCOHOL | 40 | 40 | 40 | 40 | 40 | 40 | 40 | 40 |
| | MALTITOL | 35 | — | — | — | — | — | — | — |
| | XYLITOL | — | 35 | — | — | — | — | — | — |
| | MANNITOL | — | — | 35 | — | — | — | — | — |
| | LACTITOL | — | — | — | 35 | — | — | — | — |
| | SUCROSE | — | — | — | — | 35 | — | — | — |
| | ERYTHRITOL | — | — | — | — | — | 35 | — | — |
| | SORBITOL | — | — | — | — | — | — | 35 | — |
| | ISOMALT | — | — | — | — | — | — | — | 35 |
| | TRIETHYL CITRATE | 5 | 5 | 5 | 5 | 5 | 5 | 5 | 5 |
| WEIGHT OF SOLID OBJECT(mg) Average(n = 3) | | 246 | 263 | 262 | 238 | 261 | 256 | 263 | 248 |
| HEIGHT OF SOLID OBJECT(mm) Average(n = 3) | | 2.6 | 2.7 | 2.7 | 2.4 | 2.6 | 2.6 | 2.5 | 2.7 |

TABLE 6

|  |  | EXAMPLE 5-1 ACETAMINOPHEN | EXAMPLE 5-2 THEOPHYLLINE |
|---|---|---|---|
| EACH CONSTITUENT COMPONENT (wt. %) | ACETAMINOPHEN | 20 | — |
|  | THEOPHYLLINE | — | 20 |
|  | POLYVINYL ALCOHOL | 40 | 40 |
|  | MALTITOL | 35 | 35 |
|  | TRIETHYL CITRATE | 5 | 5 |
| WEIGHT OF SOLID OBJECT (mg) Average(n = 3) |  | 267 | 252 |
| HEIGHT OF SOLID OBJECT (mm) Average(n = 3) |  | 2.7 | 2.4 |

Test Example 6: Elution Test of Active Component

The elution test was performed using the solid objects in Examples 5-1 and 5-2 in the same manner as in Test example 1 in accordance with the paddle method (the paddle rotation number: 50 rpm) of the dissolution test method in the Japanese Pharmacopoeia, Sixteenth Edition.

(Results and Discussion of Test Example 6)

Figure 7:
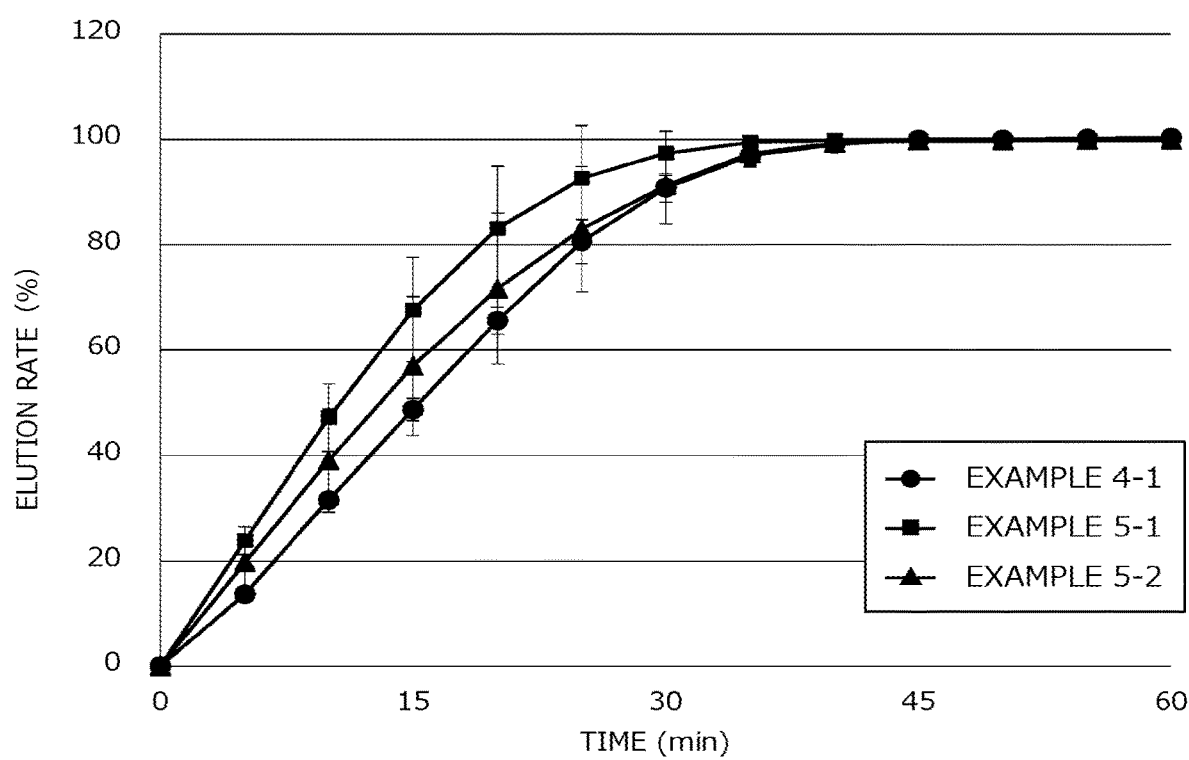
FIG. 7 is result data of the elution test in Test example 6.

On the basis of analysis of results of the elution test, a graph in FIG. 7 shows a relation between the "time (min) after starting test" and the "elution rate (%) of active component" of the solid object in each of Examples 5-1 and 5-2.

From the results in Test example 6, the solid objects in Examples 5-1 and 5-2 showed the elution rates after the lapse of 30 minutes of 97% (acetaminophen) and 91% (theophylline), respectively, confirming that the present invention could be applied to an active component other than the compound A.

Comparative Example 1: Comparison with Three-Dimensionally Molded Object Including Insoluble Component The filaments having formulation and formulation ratios shown in Table 7 were produced using tricalcium phosphate or talc as an insoluble component instead of the sugar and/or the sugar alcohol of the present invention, and the solid objects in Comparative examples 2-1 and 2-2 (n=3) were produced with the 3D printer as the three-dimensionally molded objects each including 50 mg of the active component.

Note that the ring shape 1 shown in FIG. 2B was selected as the shape in Comparative examples 2-1 and 2-2 and printing was performed on the basis of 3D CAD data in which an outer diameter of the ring was set to 12.0 mm and an inner diameter of the ring was set to 7.6 mm. A formulation ratio of each constituent component was adjusted such that the compound A as the active component became 20 wt. %, the polyvinyl alcohol became 40 wt. %, tricalcium phosphate (product name: tricalcium phosphate food additives, manufactured by KANTO CHEMICAL Co., Inc.) or talc (product name: crown talc pharmacopoeia PP, manufactured by matsumura sangyo Co., Ltd.) became 35 wt. %, and triethyl citrate became 5 wt. % with respect to 100 wt. % of the total weight.

TABLE 7

|  |  | COMPARATIVE EXAMPLE 2-1 TRICALCIUM PHOSPHATE | COMPARATIVE EXAMPLE 2-2 TALC |
|---|---|---|---|
| EACH CONSTITUENT COMPONENT (wt. %) | COMPOUND A | 20 | 20 |
|  | POLYVINYL ALCOHOL | 40 | 40 |
|  | TRICALCIUM PHOSPHATE | 35 | — |
|  | TALC | — | 35 |
|  | TRIETHYL CITRATE | 5 | 5 |
| WEIGHT OF SOLID OBJECT (mg) Average(n = 3) |  | 264 | 256 |
| HEIGHT OF SOLID OBJECT (mm) Average(n = 3) |  | 2.4 | 2.1 |

Test Example 7: Elution Test of Active Component

The elution test was performed using the solid objects in Comparative examples 2-1 and 2-2 shown in Table 7 in the same manner as in Test example 1 in accordance with the paddle method (the paddle rotation number: 50 rpm) of the dissolution test method in the Japanese Pharmacopoeia, Sixteenth Edition.

(Results and Discussion of Test Example 7)

Figure 8:
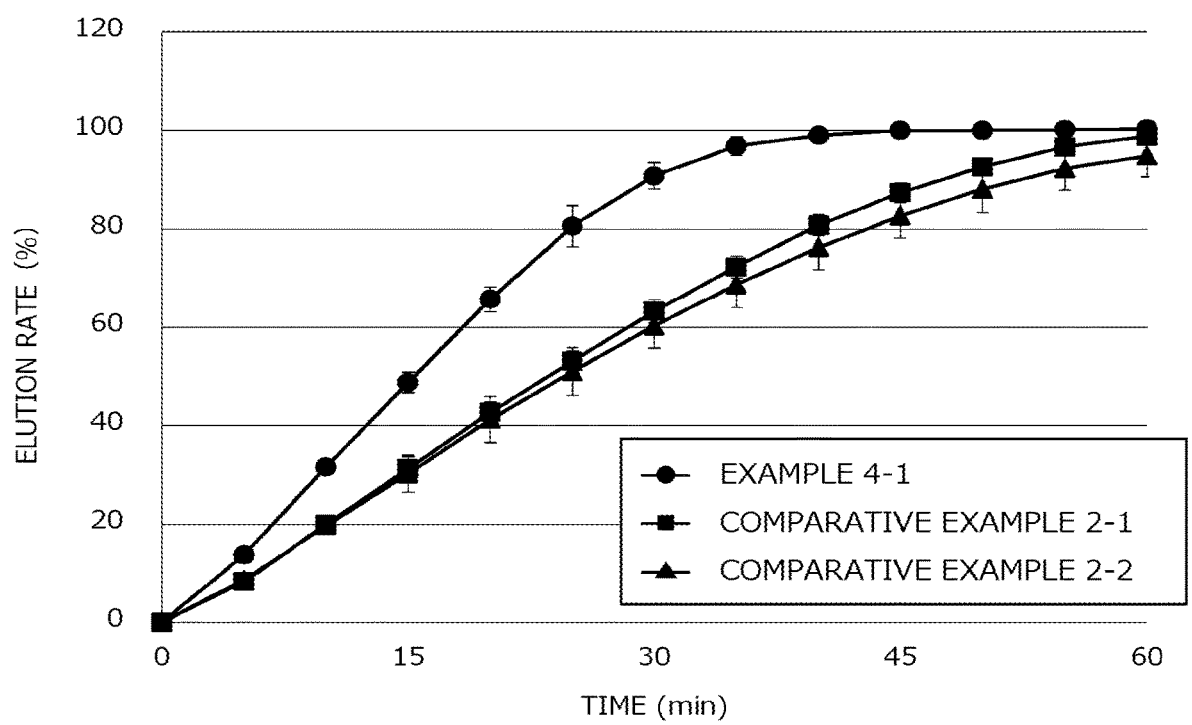
FIG. 8 is result data of the elution test in Test example 7.

On the basis of analysis of results of the above-mentioned elution test, a graph in FIG. 8 shows a relation between the "time (min) after starting test" and the "elution rate (%) of active component" of the solid object in each of Comparative examples 2-1 and 2-2.

From the results in Test example 7, it was found that the solid objects in Comparative examples 2-1 and 2-2 showed the elution rates after the lapse of 30 minutes of 63% (Comparative example 2-1: tricalcium phosphate) and 60% (Comparative example 2-2: talc), both values being lower than 80%.

Thus, it was confirmed that a formulation having a higher elution rate could be prepared by adding the sugar and/or the sugar alcohol as compared to the case where tricalcium phosphate or talc was included.

Example 6: Three-Dimensionally Molded Object Having Different Formulation Ratio of Maltitol The filament of Example 6 having formulation and a formulation ratio shown in Table 8 was produced and the solid objects (n=3) were produced with the 3D printer.

Note that the ring shape 1 shown in FIG. 2B was selected as the shape in Example 6 and printing was performed on the basis of 3D CAD data in which an outer diameter of the ring was set to 12.0 mm and an inner diameter of the ring was set to 7.6 mm. A formulation ratio of each constituent component was adjusted such that the compound A as the active component became 20 wt. %, the polyvinyl alcohol became 55 wt. %, maltitol became 20 wt. %, and triethyl citrate became 5 wt. % with respect to 100 wt. % of the total weight.

A as the active component became 20 wt. %, the thermoplastic polymer became 40 wt. %, maltitol became 35 wt. %, and triethyl citrate became 5 wt. % with respect to 100 wt. % of the total weight.

The filament produced by using polyvinylpyrrolidone tended to be more fragile as compared to the one produced by using the polyvinyl alcohol.

TABLE 9

| | | EXAMPLE 7-1 POLYVINYLPYRROLIDONE | EXAMPLE 7-2 AMINOALKYL METHACRYLATE COPOLYMER E |
|---|---|---|---|
| EACH CONSTITUENT COMPONENT (wt. %) | COMPOUND A | 20 | 20 |
| | POLYVINYLPYRROLIDONE | 40 | — |
| | AMINOALKYL METHACRYLATE COPOLYMER E | — | 40 |
| | MALTITOL | 35 | 35 |
| | TRIETHYL CITRATE | 5 | 5 |

TABLE 8

| | | EXAMPLE 6 MALTITOL 20 wt. % |
|---|---|---|
| EACH CONSTITUENT COMPONENT (wt. %) | COMPOUND A | 20 |
| | POLYVINYL ALCOHOL | 55 |
| | MALTITOL | 20 |
| | TRIETHYL CITRATE | 5 |
| WEIGHT OF SOLID OBJECT (mg) Average(n = 3) | | 229 |
| HEIGHT OF SOLID OBJECT (mm) Average(n = 3) | | 2.4 |

Test Example 8: Elution Test of Active Component

Figure 9:
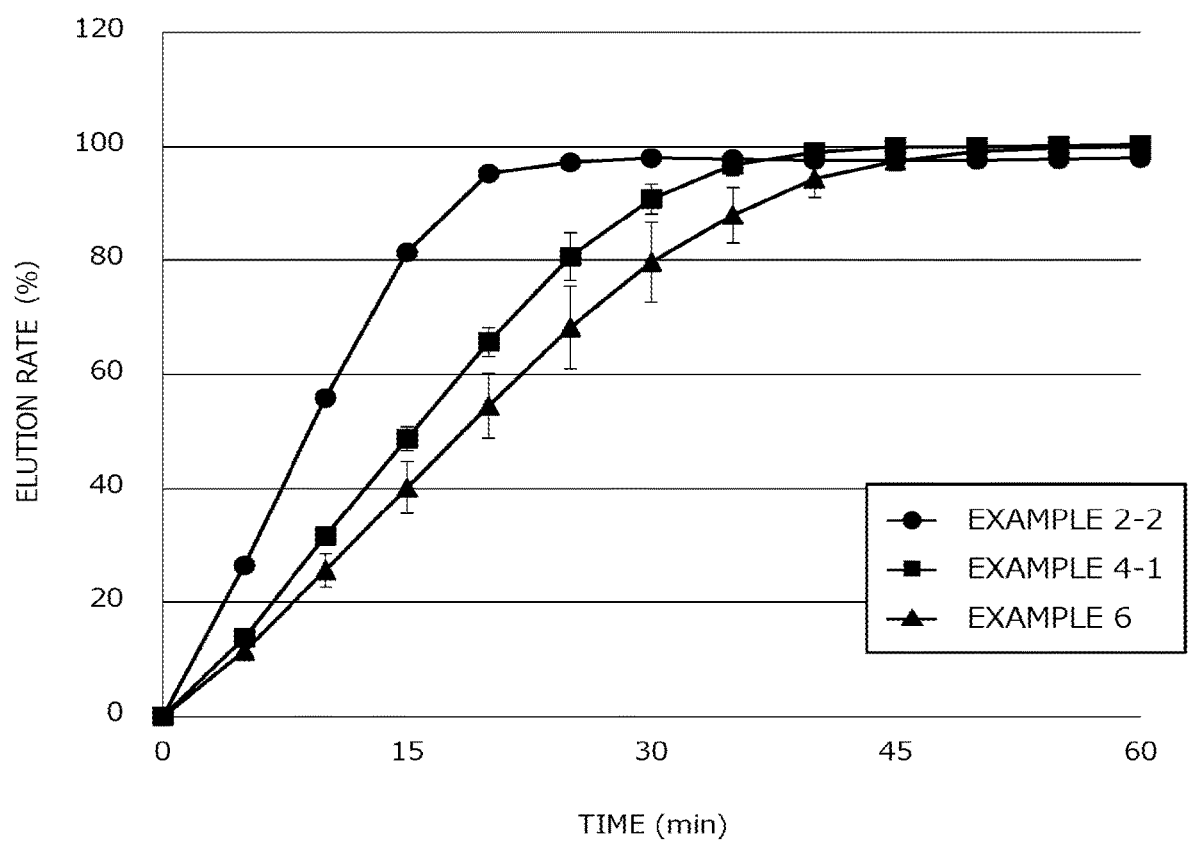
FIG. 9 is result data of the elution test in Test example 8.

The elution test was performed using the solid object in Example 6 shown in Table 8 in the same manner as in Test example 1 in accordance with the paddle method (the paddle rotation number: 50 rpm) of the dissolution test method in the Japanese Pharmacopoeia, Sixteenth Edition.
(Results and Discussion of Test Example 8)
On the basis of analysis of results of the above elution test, a graph in FIG. 9 shows a relation between the "time (min) after starting test" and the "elution rate (%) of active component" of the solid object in Example 6.

From the result in Test example 8, it was confirmed that the solid object in Example 6 showed the elution rate after the lapse of 30 minutes of 80%. It was found that the elution rate increased by an increase in the addition amount of maltitol by comparing the elution rates obtained with the above formulation, the formulation in Example 2-2 in which maltitol was added in the amount of 55 wt. %, and the formulation in Example 4-1 in which maltitol was added in the amount of 35 wt. %.

Example 7: Three-Dimensionally Molded Objects Including Different Thermoplastic Polymers The filaments in Examples 7-1 and 7-2 having formulation and formulation ratios shown in Table 9 were produced by selecting polyvinylpyrrolidone (Polyvinylpyrrolidone [Mw40000], manufactured by Sigma Aldrich) or aminoalkyl methacrylate copolymer E (Eudragit EPO, manufactured by Evonik Industries AG) instead of the polyvinyl alcohol as the thermoplastic polymer. A formulation ratio of each constituent component was adjusted such that the compound Test Example 9: Elution Test of Active Component The elution test was performed using the filaments in Examples 7-1 and 7-2 shown in Table 9, the filament including the polyvinyl alcohol and maltitol produced in Example 4-1, and the filament including the polyvinyl alcohol and tricalcium phosphate produced in Comparative example 2-1 in the same manner as in Test example 1 in accordance with the paddle method (the paddle rotation number: 50 rpm) of the dissolution test method in the Japanese Pharmacopoeia, Sixteenth Edition.

Figure 10:
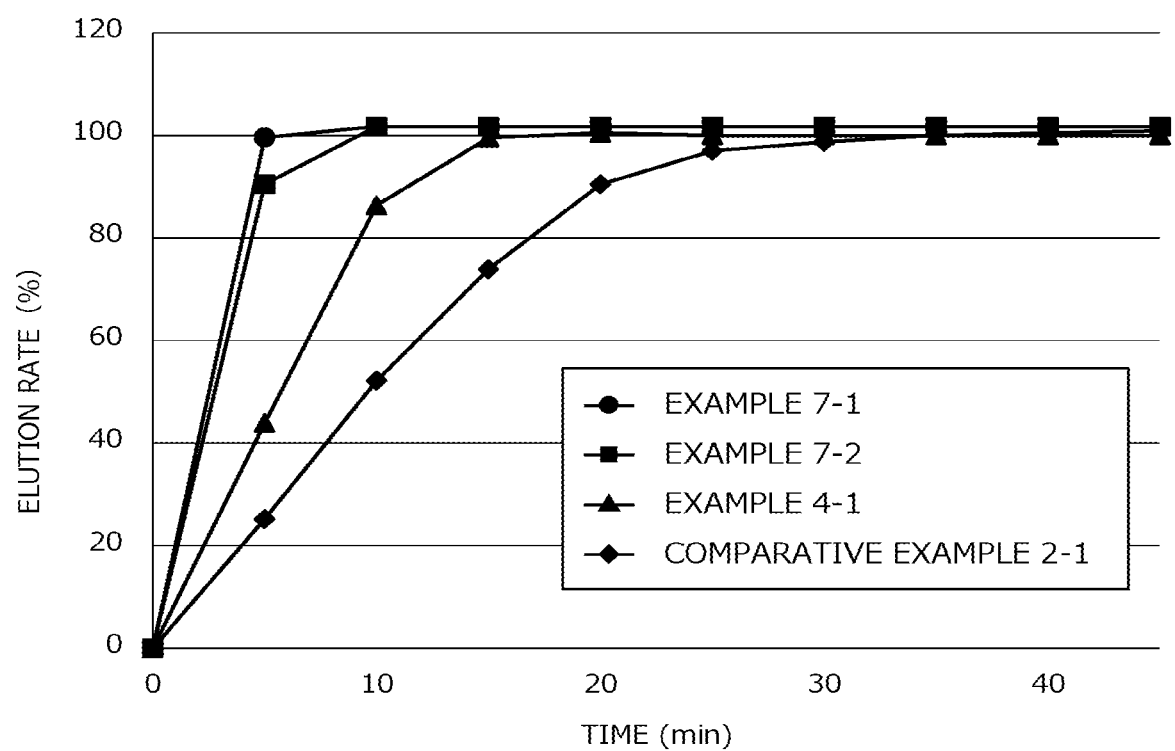
FIG. 10 is result data of the elution test in Test example 9.

Note that each filament in use included the compound A having a weight of 50 mg as the active component.
(Results and Discussion of Test Example 9)
On the basis of analysis of results of the elution test, a graph in FIG. 10 shows a relation between the "time (min) after starting test" and the "elution rate (%) of active component" of the filament in each of Examples 4-1, 7-1, and 7-2, and Comparative example 2-1.

From the results in Test example 9, the filaments in Examples 7-1 and 7-2 showed the elution rates after the lapse of 5 minutes of 100% (Example 7-1: polyvinylpyrrolidone) and 91% (Example 7-2: aminoalkyl methacrylate copolymer E). The filament including the polyvinyl alcohol and maltitol in Example 4-1 and the filament including the polyvinyl alcohol and tricalcium phosphate in Comparative example 2-1 had the elution rates after the lapse of 5 minutes of 44% and 25%, respectively, thus it was found that the fast elutability was exhibited in the formulation in Examples 7-1 and 7-2 in which polyvinylpyrrolidone and aminoalkyl methacrylate copolymer E were used.

<Solid Object in Example 7-1: Three-Dimensionally Molded Object Using Polyvinylpyrrolidone>

The solid objects in Example 7-1 (n=3) were produced with the 3D printer using the filament produced in Example 7-1.

Note that the ring shape 1 shown in FIG. 2B was selected as the shape of the solid object in Example 7-1 and printing was performed on the basis of 3D CAD data in which an outer diameter of the ring was set to 12.0 mm and an inner diameter of the ring was set to 7.6 mm. A weight of a printed object and a height of the solid object were shown in Table 10.

TABLE 10

|  | EXAMPLE 7-1 POLYVINYLPYRROLIDONE/ MALTITOL 35% |
| --- | --- |
| WEIGHT OF SOLID OBJECT (mg) Average(n = 3) | 249 |
| HEIGHT OF SOLID OBJECT (mm) Average(n = 3) | 2.5 |

Test Example 10: Elution Test of Active Component

The elution test was performed using the solid object in Example 7-1 in the same manner as in Test example 1 in accordance with the paddle method (the paddle rotation number: 50 rpm) of the dissolution test method in the Japanese Pharmacopoeia, Sixteenth Edition.
(Results and Discussion of Test Example 10)

Figure 11:
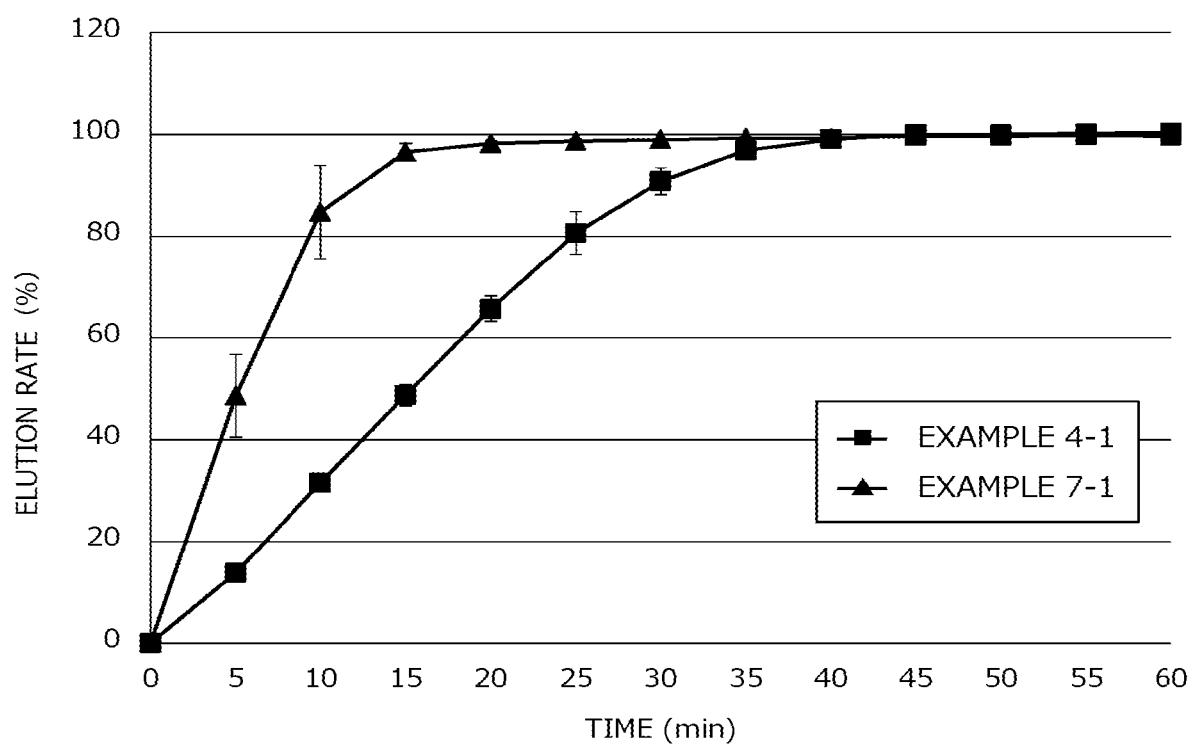
FIG. 11 is result data of the elution test in Test example 10.

On the basis of analysis of results of the elution test, a graph in FIG. 11 shows a relation between the "time (min) after starting test" and the "elution rate (%) of active component" of the solid object in Example 7-1. FIG. 11 also showed the graph of the solid object in Example 4-1.

From the results in Test example 10, it was confirmed that the solid object in Example 7-1 showed the elution rate after the lapse of 30 minutes of 99%.

INDUSTRIAL APPLICABILITY

The three-dimensionally molded object of the present invention can be suitably used as various molded objects for a pharmaceutical agent, a quasi-drug, a health food, a food for specified health uses, a food with nutrient function claims, a food with function claims, and a supplement, and thus has an industrial applicability.

The invention claimed is:

1. A method for making a fast-eluting three-dimensionally (3-D) molded object by fused deposition modeling, the method comprising:
   admixing an active component with a water-soluble thermoplastic polymer, a water-soluble sugar and/or a water-soluble sugar alcohol, and a plasticizer component to form a material for a 3-D molded object, wherein the water-soluble sugar and/or the water-soluble sugar alcohol is selected from a group consisting of maltitol, xylitol, mannitol, erythritol, sorbitol, and lactitol;
   compressing and melt-kneading the material for a 3-D molded object in an extruder to form an extruded material;
   subjecting the extruded material to injection molding to produce a filament; and
   extruding the filament and molding a fast-eluting 3-D molded object by lamination on a 3-D molding stage by fused deposition modeling (FDM).

2. The method according to claim 1, wherein an elution rate of the active component by a paddle method of a dissolution test method in the Japanese Pharmacopoeia, Sixteenth Edition, is 80% or higher within 85 minutes.

3. The method according to claim 1, wherein the water-soluble sugar and/or the water-soluble sugar alcohol has a glass transition temperature of a room temperature or higher.

4. The method according to claim 1, wherein the water-soluble sugar alcohol is maltitol.

5. The method according to claim 1, wherein the water-soluble thermoplastic polymer is one or more kinds selected from a group consisting of a polyvinyl alcohol, a polyvinyl caprolactam-polyvinyl acetate-polyethylene glycol graft copolymer, polyethylene oxide, polyvinylpyrrolidone, copolyvidone, a polyethylene glycol-polyvinyl alcohol-graft copolymer, a polyvinyl alcohol-acrylic acid-methyl methacrylate copolymer, and aminoalkyl methacrylate copolymer.

6. The method according to claim 1, wherein the water-soluble thermoplastic polymer is one or more kinds selected from a group consisting of a polyvinyl alcohol, polyvinylpyrrolidone, and aminoalkyl methacrylate copolymer.

7. The method according to claim 1, wherein the water-soluble thermoplastic polymer is one or more members selected from a group consisting of a polyvinyl alcohol, polyvinylpyrrolidone, and aminoalkyl methacrylate copolymer; and the water-soluble sugar and/or the water-soluble sugar alcohol is maltitol.

8. The method according to claim 1, wherein a content of the water-soluble sugar and/or the water-soluble sugar alcohol is 10 to 65 wt. % with respect to a total weight of the three-dimensionally molded object.

9. The method according to claim 1, wherein a content of the water-soluble thermoplastic polymer is 20 to 90 wt. % with respect to the total weight of the three-dimensionally molded object.

10. The method according to claim 1, wherein the elution rate of the active component is 80% or higher within 30 minutes.

11. The method according to claim 1, wherein the fast-eluting three-dimensionally molded object is a ring-shaped solid object.

12. The method according to claim 1, wherein the active component is $N^2$-[(2E)-3-(4-chlorophenyl)-2-propenoyl]-N-[2-oxo-2-(4-{[6-(trifluoromethyl)pyrimidine-4-yl]oxy}piperidine-1-yl)ethyl]-3-pyridine-2-yl-L-alaninamide.

13. The method according to claim 1, wherein the water-soluble thermoplastic polymer is a polyvinyl alcohol;
   the water-soluble sugar and/or the water-soluble sugar alcohol is one or more kinds selected from a group consisting of sucrose, maltitol, xylitol, mannitol, erythritol, sorbitol and lactitol; and a content of the active component is 0.1 to 20 wt %;
   a content of the water-soluble thermoplastic polymer is 20 to 55 wt %; and
   a content of the water-soluble sugar and/or the water-soluble sugar alcohol is 20 to 55 wt % with respect to a total weight of the material.

* * * * *